United States Patent
Schary et al.

(10) Patent No.: US 6,952,841 B2
(45) Date of Patent: Oct. 11, 2005

(54) SPORTS GOGGLES

(75) Inventors: Philippe Schary, Groisy (FR); Pierre Desarmaux, La Cote (FR)

(73) Assignee: Salomon S.A., Metz-Tessy (FR)

( * ) Notice: Subject to any disclaimer, the term of this patent is extended or adjusted under 35 U.S.C. 154(b) by 233 days.

(21) Appl. No.: 10/413,397

(22) Filed: Apr. 15, 2003

(65) Prior Publication Data

US 2003/0221246 A1 Dec. 4, 2003

(30) Foreign Application Priority Data

Apr. 16, 2002 (FR) .............................. 02 05020

(51) Int. Cl.⁷ .................................................. A61F 9/02
(52) U.S. Cl. ........................................................ 2/452
(58) Field of Search .......................... 2/446, 448, 450, 2/452; 128/857, 858; 351/111–114, 118, 150, 123

(56) References Cited

U.S. PATENT DOCUMENTS

| | | | | |
|---|---|---|---|---|
| 2,758,308 A | | 8/1956 | Ellis ................................. | 2/14 |
| 3,660,852 A | * | 5/1972 | Schulenberg ..................... | 2/12 |
| 4,391,498 A | * | 7/1983 | Rengstorff ..................... | 351/111 |
| 4,723,844 A | * | 2/1988 | Medina ........................ | 351/114 |
| 5,042,933 A | * | 8/1991 | Lear ............................ | 351/111 |
| 5,302,977 A | * | 4/1994 | Markovitz et al. ........... | 351/114 |
| 5,413,119 A | * | 5/1995 | Guerrant ..................... | 128/858 |
| 5,706,527 A | | 1/1998 | Kita et al. ..................... | 2/452 |
| 6,817,068 B2 | * | 11/2004 | Cleary et al. ................. | 24/3.13 |

FOREIGN PATENT DOCUMENTS

| | | |
|---|---|---|
| GB | 530312 | 12/1940 |
| GB | 921203 | 3/1963 |

OTHER PUBLICATIONS

U.S. Design Patent Application No. 29/178,884 (Borlet et al.), filed on Apr. 2, 2003.

\* cited by examiner

*Primary Examiner*—Katherine M. Moran
(74) *Attorney, Agent, or Firm*—Greenblum & Bernstein, P.L.C.

(57) ABSTRACT

Goggles having a frame with two lateral edges, a shield borne by the frame, and a tie for retaining the frame on the user's head which is attached to each of the lateral edges of the frame. The tie for retaining the frame has a flexible cord located at each of the ends of the tie, each of the cords being connected to the frame by two upper and lower pull points separated along a lateral edge according to an upper cord strand and a lower cord point, and a return element sliding along the cord to allow the respective lengths of the upper and lower cord strands to be modified.

12 Claims, 4 Drawing Sheets

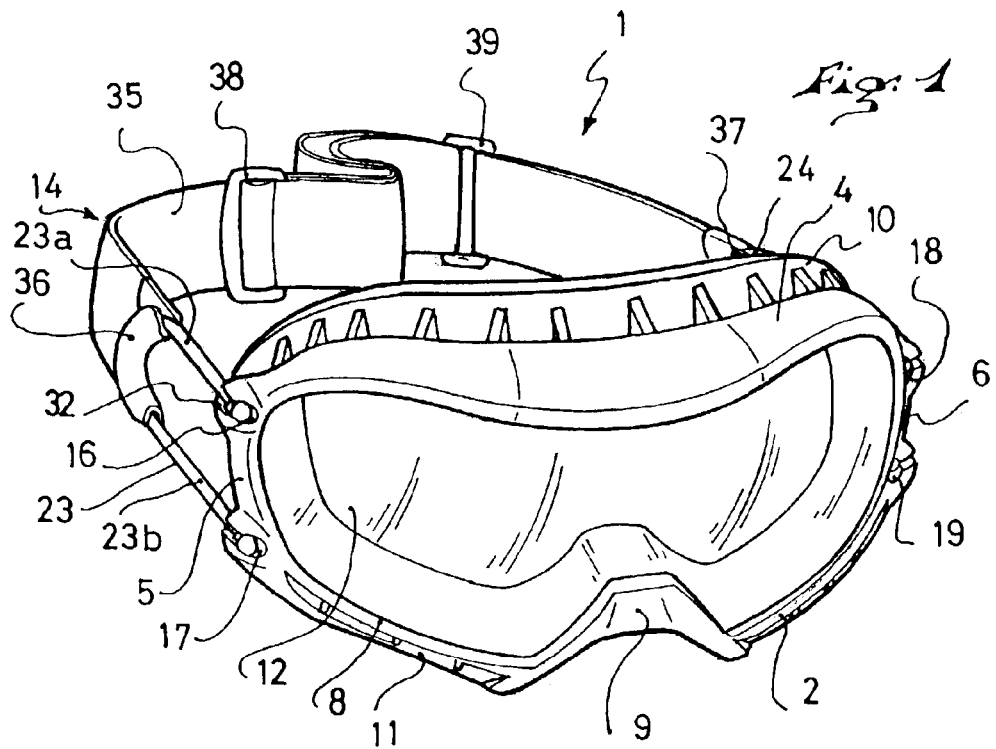
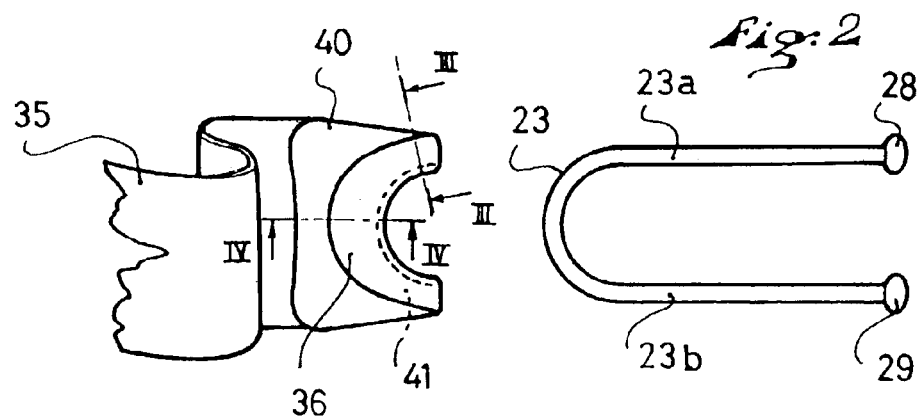

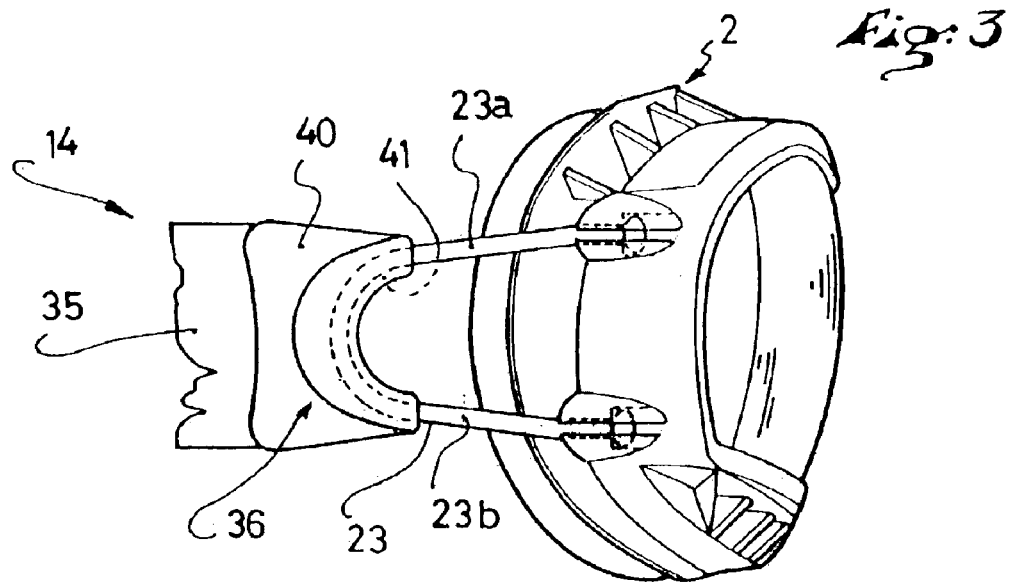
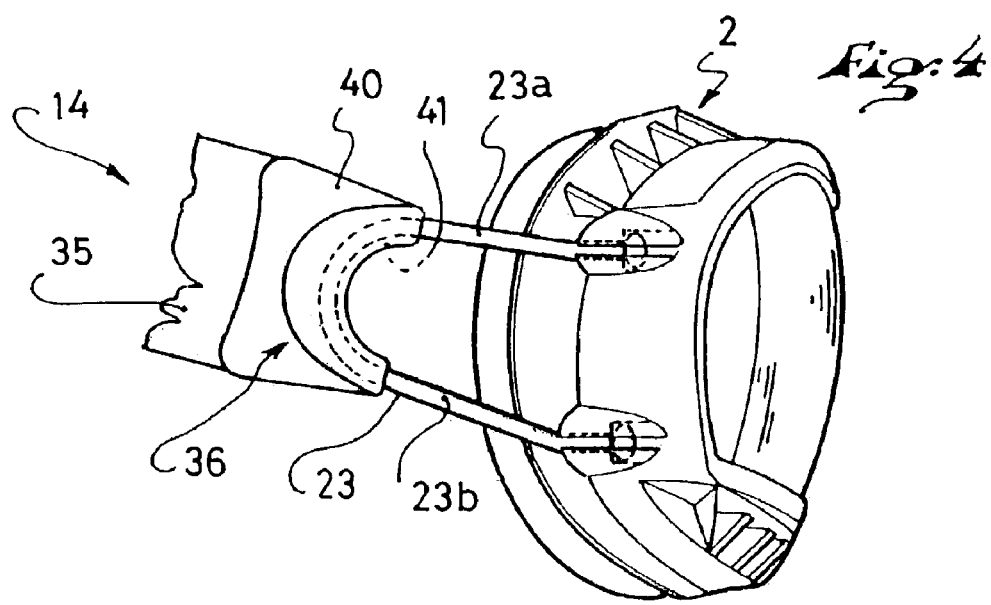

SPORTS GOGGLES

CROSS-REFERENCE TO RELATED APPLICATION

This application is based upon French Patent Application No. 02.05020, filed Apr. 16, 2002, the disclosures of which is hereby incorporated by reference thereto in its entirety, and the priority of which is hereby claimed under 35 U.S.C. §119.

BACKGROUND OF THE INVENTION

1. Field of the Invention

The present invention relates to goggles. More particularly, the invention relates to protective facial goggles such as those that are used, for example, in the sports of skiing or motorcycling.

2. Description of Background and Relevant Information

For skiing, in particular, it is known to use goggles having a frame, a protective shield, and a wide elastic strap that surrounds the head.

One of the problems of these types of goggles is the pressure exerted by the frame on the face. This pressure depends on the morphology of the user's face, the tension of the elastic strap, and its position on the head.

In particular, if the elastic strap is angularly offset with respect to a plane that is perpendicular to the plane defined by the frame, the pressure of the frame is not exerted evenly on the face.

In order to overcome this drawback, it is known to connect the elastic strap to the frame, not by a fixed fastener, but by a pivoting fastener that is located toward the middle of the height of the frame.

This allows for a better distribution of the pressure. Nevertheless, there is still a noticeable concentration of the pressure exerted by the frame on the face in the area of the points for fastening the strap.

SUMMARY OF THE INVENTION

An object of the invention is to improve the comfort of protective goggles through an even better controlled distribution of pressure of the frame on the face.

Another object of the invention is to propose goggles in which the user can adjust the distribution of pressure himself and possibly memorize it.

Other objects and advantages of the invention will become apparent from the following description.

The goggles according to the invention have a frame with two lateral edges, a shield borne by the frame, and a tie for retaining the frame on the user's head which is attached to each of the lateral edges of the frame.

The tie for retaining the frame has a flexible cord located at each of the ends of the tie, each of the cords being connected to the frame by two upper and lower pull points that are spaced apart along a lateral edge according to an upper cord strand and a lower cord point, and a return element sliding along the cord to allow the respective lengths of the upper and lower strands of the cord to be modified.

BRIEF DESCRIPTION OF DRAWINGS

The invention will be better understood with reference to the following description and to the attached drawings, in which:

FIG. 1 is an overall perspective view of a pair of goggles according to a first embodiment of the invention;

FIG. 2 shows the end of the band and the cord before fastening;

FIGS. 3 and 4 show the functioning of this embodiment;

DETAILED DESCRIPTION OF THE INVENTION

Figure 5:
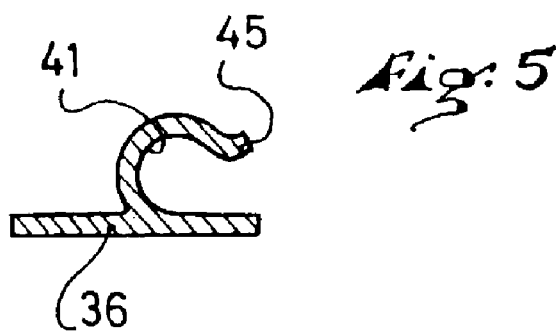
FIGS. 5 and 6 relate to alternative constructions.

FIG. 1 shows, in perspective, a pair of goggles 1 according to a first non-limiting embodiment of the invention.

The goggles have a frame 2. The frame is of any type and any appropriate form. For instance, the frame 2 can be made of plastic, and it can have a closed mounting with an elongated form with an upper bar 4, two lateral sides 5 and 6, a lower bar 8 having a median nose bridge 9 provided to rest on the user's nose.

On its rear surface, the frame 2 has, in the illustrated embodiment, a sealing lip or ring 10 for contact with the user's face, possibly bordered with an elastically deformable foam to improve comfort.

As an option, the frame can have air vents 11 at the front, at the bottom and/or at the top of the frame.

In a conventional manner, the frame has a shield 12 that is retained in a holding groove. The shield can be of any appropriate type, and it can made of any currently known material. In particular, the shield can be single or double, and it can be made from a cut sheet or by molding. It can be transparent, tinted or non-tinted.

A retaining tie 14 is furthermore attached to the frame to retain the goggles in place on the user's head.

According to the embodiment shown, each of the sides, or lateral edges, 5 and 6 of the frame has pull points 16, 17 for the edge 5, and 18, 19 for the edge 6, which are spaced apart from each other.

These pull points are each provided to retain the ends of two flexible cords 23 and 24 that are located at the ends of the retaining tie.

The pull points are spaced along the lateral edges 5 and 6 of the frame to distribute the forces of traction exerted by the tie on the frame. For adult-sized goggles, good results can be obtained from a spacing of the points equal to or greater than 30 millimeters, or between 30–40 millimeters and, for example, equal to 35 millimeters. These values are not to be considered limiting to the invention, as other sizes are envisioned. Because the frame is retained by the cords 23 and 24, the pull points are shown to remain in the area of the lateral edges, and they are not located in the area of the bars.

Further, the two pull points of a lateral edge are offset toward the upper bar and are closer to the upper bar than the lower bar.

According to the example shown, the cords are attached to the frame by their ends. For the cord 23, for example, this can be seen in FIG. 2 where the ends of the cord have an enlargement, or bulge 28, 29. This bulge can be made in different manners, for example, it is formed by a knot of the cord itself, or by an attached sleeve that is crimped or welded to the cord, or yet in the case where the cord is made of a synthetic material, it can be formed by melting and shaping the ends. Other techniques are also applicable.

In order to retain the cords 23 and 24, the pull points, for example, are shouldered housings made by molding on the lateral edges of the frame. The cord extends right through the housing, and its end bulge is retained by the shoulder. In this case, a lateral slit is provided through which the cord is positioned in the housing. Such a slit bears the reference number 32 for the pull point 16.

Other constructional embodiments can also be appropriate. For example, one could provide holes traversing the lateral edges of the frame, possibly with housings in which to house knots made at the ends of the cords.

The cords 23, 24 can be made of any appropriate flexible material. According to the present embodiment, the cords are not extensible, or only slightly. For example, the cords can be braided from synthetic and/or natural textile fibers. According to another possibility, the cords can be formed by a flexible plastic ring. The cross-section of the cords is not necessarily constant, and one could provide, for example, a sheathing in its zone of friction with the return element that will be described below.

The lengths of either cord is not limiting to the invention. The cord must be enough to offset its point of fastening to the return piece toward the rear of the goggles.

The cords are connected to an elastically extensible band 35 by return elements 36 and 37.

The extensible band 35 is of any appropriate type and of any appropriate width, whether constant or not. Keepers 38 and 39 can be used, as shown in the illustrated embodiment, between which the tie 14 is diverted by loops, to enable length adjustability of the band 35.

According to the embodiment shown, each return element, particularly the element 36 shown in FIG. 2, has a plate 40 for connecting with the end of the extensible band 35. The plate can be sewn, welded, or glued, for example, to the end of the band, or assembled through another technique.

Furthermore, the element 36 has a return channel 41 that is curved inward over approximately a half-circle, with its two ends located on the side of the frame. The dimensions of the channel 41 in cross-section are sufficient for receiving the cord by allowing it to slide.

According to the embodiment shown, the channel 41 almost forms a half-circle whose diameter is approximately equal to the distance between the pull points. This is not limiting to the invention, and the opening angle formed by the channel could be different. Also, the channel could have a form other than a circular form, and the distance between its ends could be different from the spacing between the pull points 16, 17 of the frame. However, according to the invention, the channel 41 should be capable of receiving the flexible cord 23 in order to be guided along a return loop, and that it allows the flexible tie to slide. The return loop separates the cord into two strands, an upper strand 23a and a lower strand 23b.

The return elements 36, 37 can be made of any appropriate material, particularly plastic.

One can possibly equip the return elements 36, 37 with a layer of foam, or a textile layer for protecting the ears.

However, this is not limiting to the invention, and the return elements 36, 37 can also be sized so as not to be supported directly upon the ears.

FIGS. 3 and 4 show the functioning of this constructional embodiment.

One can see from these two drawing figures that the orientation of the retaining tie 14 with respect to the frame 2 has been modified. This change in orientation results from the sliding of the cord 23 in the channel 41 of the return element 36, which has modified the respective length of the upper 23a and lower 23b strands of the cord 23.

This change in orientation allows the goggles to be adjusted to the particular shape, or morphology, of the user's face in order to balance the pressure between the top or the bottom of the goggles or, on the contrary, to modify this distribution. The user also has the possibility of orienting the tie 14 as he/she wishes with respect to the frame 2.

The sliding of the cords 23, 24 in the return elements 36, 37 allows this adjustment between the tie 14 and the frame 2 of the goggles. The retracted position of the return elements with respect to the frame and the spacing of the pull points 16, 17 give a good distribution of the pressure from the frame on the user's face.

In addition, when necessary, it is possible to remove the goggles by unfastening one of the cords 23, 24 from its return element.

Figure 6:
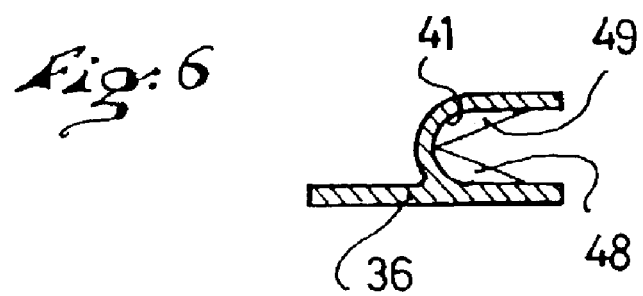

FIGS. 5 and 6 show alternative constructions of the channel.

According to FIG. 5, the channel 41 has an opening that is closed by an edge 45. With the edge, a hard spot must be cleared when the cord is inserted into or extracted from the channel, this hard spot being created by the deformation of the channel or the compression of the cord.

The edge can be present over the entire length of the channel, or only over a portion of its length. For example, one could have this edge in the area of the two ends of the channel. Other means can also be appropriate to obtain the effect of a hard spot between the cord and its return channel.

According to FIG. 6, the back of the channel 41 has, at least locally, converging ridges 48, 49 whose purpose is to pinch the cord when it is drawn toward the back of the channel.

This allows memorizing a positioning adjustment for the goggles by preventing a sliding of the cord. The adjustment is then kept even if the goggles are removed.

Other means, for example, projecting points, could also be appropriate for immobilizing the cord in the channel.

As an alternative to this embodiment, one could use extensible cords having an extensible band, or even an inextensible band.

Figure 7:
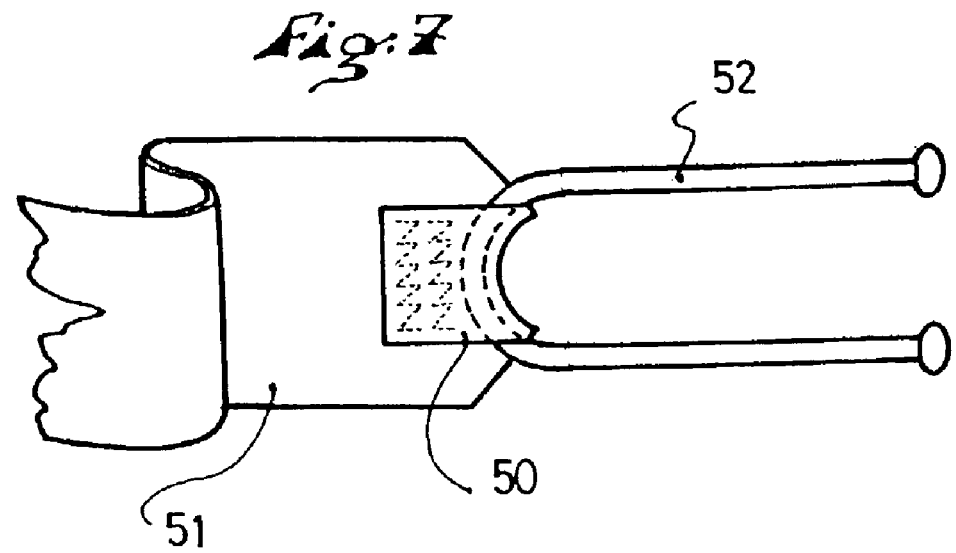
FIG. 7 shows an alternative embodiment of the invention.

FIG. 7 shows another alternative embodiment. According to this embodiment, the end of the band 51 is folded back over the rest of the band to form a flap 50 that is assembled to the rest of the band, for example, by stitching.

In the embodiment shown, the flap is narrower than the rest of the band, but this is not limiting.

The loop formed by the end of the band with its flap constitutes a return element in which the cord 52 is engaged with a possibility of sliding.

Figure 8:
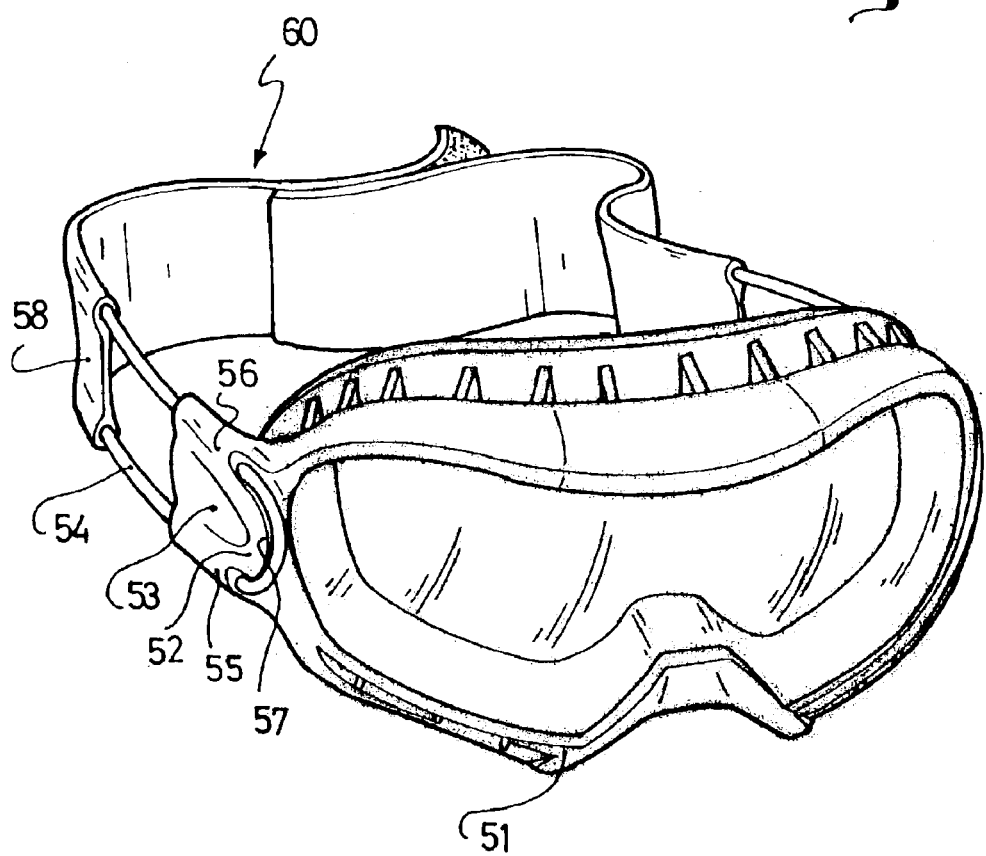
FIG. 8 shows another embodiment of the invention.

FIG. 8 pertains to another alternative embodiment. Instead of being attached to the retaining tie, the return element here is part of the frame.

To this end, as shown in FIG. 8, each of the lateral edges of the frame 51 has a return element 52 allowing the passage and sliding of a flexible cord 54. The return element is advantageously integrated into the structure of the frame. For example, as seen in the FIG. 8, each lateral edge, particularly the edge 53, has two channels or conduits 55 and 56 that traverse the lateral edge in a rear-to-front direction, and that are connected at the front by a curved guiding channel or track 57. The channels or conduits 55, 56 have cross-sections whose dimensions are greater than those of the flexible tie. In this manner, the flexible tie 54 traverses the two channels 55 and 56 that form the pull points, and it follows the guiding track with a possibility of free sliding.

Toward the rear, the two ends of the cord are connected, for example, to a band 58, by any appropriate means, for example, by stitching.

According to the embodiment shown, the band 60 is inextensible. It is formed of two parts that are detachably assembled together, and adjustable in length by means of a hook-and-loop fastener that is commercially known as "VELCRO."

Preferably, in this case, the cords are elastically extensible. This is not limiting, the band could be extensible as in the previous case and adjustable in length by means of keepers. The cords could also be inextensible.

According to another alternative, the flexible cords could be connected to each other in a continuous manner to form the retaining tie, i.e., in this hypothesis, the band would no longer exist.

In the area of the frame, the return elements could also be made differently.

As in the previous case, it is possible to modify the relative orientation between the retaining tie and the frame by causing the sliding of the return elements along the cords to modify the respective length of its upper and lower strands.

As in the previously described case, one could have edges to confine the cord in the guiding track and/or ridges or projecting points in order to immobilize it.

The present description is given only by way of example, and one could use other embodiments of the invention without leaving the scope thereof.

Lastly, the invention is not limited to goggles for skiing or motorcycling, and it can be applied to other fields, such as diving masks, for example.

What is claimed is:

1. Goggles comprising:
   a frame having a pair of opposite lateral edges;
   a shield borne by the frame;
   a tie retaining the frame on a user's head, said tie being attached to each of the lateral edges of the frame, said tie having a flexible cord located at each of opposite ends of said tie, each of said cords being connected to the frame by two upper and lower pull points spaced apart along a lateral edge at an upper cord point and a lower cord point, and a return element slidable along said cord to allow respective lengths of said upper and lower cord strands to be modified.

2. Goggles according to claim 1, wherein the upper and lower pull points are separated by 30–40 millimeters along the lateral edges of the frame.

3. Goggles according to claim 1, wherein each of the return elements has an inward curved channel in which a respective one of said cords is engaged.

4. Goggles according to claim 1, wherein the retaining tie comprises a band, and wherein the return elements are located at the ends of the band.

5. Goggles according to claim 1, wherein the cords are attached by bulged ends.

6. Goggles according to claim 4, wherein the bulged ends are housed in shouldered housings made in the lateral supports of the frame.

7. Goggles according to claim 1, wherein the tie comprises a band whose ends are folded along a flap to form a loop in which the cord is engaged with a possibility for sliding.

8. Goggles according to claim 1, wherein each of the return elements is a guiding track formed in the lateral edges of the frame.

9. Goggles according to claim 8, wherein the ends of the cords are attached to the ends of a band.

10. Goggles according to claim 8, wherein the cords are connected together in a continuous manner.

11. Goggles according to claim 1, wherein the upper and lower pull points are separated by more than 30 millimeters along the lateral edges of the frame.

12. Goggles according to claim 1, wherein the upper and lower pull points are separated by 35 millimeters along the lateral edges of the frame.

* * * * *